United States Patent [19]
Krag et al.

[11] Patent Number: 5,219,349
[45] Date of Patent: Jun. 15, 1993

[54] SPINAL FIXATOR REDUCTION FRAME

[75] Inventors: Martin H. Krag, Colchester, Vt.; John S. Crombie, Irvington, N.J.

[73] Assignee: Howmedica, Inc., New York, N.Y.

[21] Appl. No.: 657,024

[22] Filed: Feb. 15, 1991

[51] Int. Cl.[5] .............................................. A61F 5/01
[52] U.S. Cl. ..................................... 606/53; 606/54; 606/105
[58] Field of Search ...................... 606/53, 54, 55, 56, 606/57, 58, 59, 86, 105

[56] References Cited

U.S. PATENT DOCUMENTS

| | | | |
|---|---|---|---|
| 2,393,694 | 1/1946 | Kirschner | 128/84 |
| 3,865,105 | 2/1975 | Lode | 128/69 |
| 4,433,677 | 2/1984 | Ulrich et al. | 128/69 |
| 4,445,513 | 5/1984 | Ulrich et al. | 128/69 |
| 4,611,580 | 9/1986 | Wu | 128/69 |
| 4,658,809 | 4/1987 | Ulrich et al. | 128/92 |
| 4,733,657 | 3/1988 | Kluger | 128/92 |
| 4,854,304 | 8/1989 | Zielke | 128/69 |
| 4,890,631 | 1/1990 | Hardy | 606/59 |
| 4,920,959 | 5/1990 | Witzel et al. | 606/53 |
| 4,929,247 | 5/1990 | Rayhack | 606/53 |
| 4,944,743 | 7/1990 | Gotzen et al. | 606/61 |

FOREIGN PATENT DOCUMENTS

| | | | |
|---|---|---|---|
| 633174 | 11/1982 | Switzerland. | |
| 475995 | 11/1975 | U.S.S.R. | 606/53 |
| 9002527 | 3/1990 | World Int. Prop. O. | 606/61 |

OTHER PUBLICATIONS

Dick et al., *A New Device for Internal Fixation of Thoracolumbar and Lumbar Spine Fractures:* The 'Fixateur Interne', Paraplegia, vol. 23, p. 230 (1985).
Dick, *Internal Fixation of Thoracic and Lumbar Spine Fractures*, pp. 95, 98 (1989).
Scoliosis Research Society and North American Spine Society, *Pedicle Fixation of the Lumbar Spine: Hands-On Surgical Skills Workshop*, pp. 6–7 and Figure 11 (Apr. 29, 1990).
The "*Fixateur Interne*", as a Versatile Implant for Spine Surgery, Spine, vol. 12, No. 9, pp. 882–900 (1987).
Olerud et al., *Transpedicular Fixation of Thoracolumbar Vertebral Fractures*, Clinical Orthopaedics and Related Research, No. 227, pp. 44–51 (Feb. 1988).
Guyer et al., The Wiltse Pedicle Screw Fixation System, Orthopaedics vol. 11, No. 10, pp. 1455–60 (Oct. 1988).
Krag et al., An Internal Fixator for Posterior Application to Short Segments of the Thoracic, Lumbar or Lumbosacral Spine, Clinical Orthopaedics and Related Research, No. 203, pp. 75–98 (Feb. 1986).

*Primary Examiner*—Robert A. Hafer
*Assistant Examiner*—Sam Rimell
*Attorney, Agent, or Firm*—Pennie & Edmonds

[57] ABSTRACT

A reduction frame according to the present invention is secured to shaft handles extending from the pedicle screws of a Vermont Spinal Fixator type implant. Shaft clamps secure two T-handles of the reduction frame to the shaft handles. A lower-rod assembly joins the two opposite T-frames by means of lower-rod clamps. The shaft clamps are provided with four degrees of freedom. The joint between the lower-rod assembly and T-handle is provided with five degrees of freedom. The lower-rod assembly and the T-handle are provided with power screw threads to allow for precise translational control. The shaft clamps and lower-rod clamps are provided with taper fit joints to allow for infinite rotational adjustment and fixture. An upper-rod assembly is also provided on the T-handles to produce rotation of the T-handles by providing means for changing the distance between the upper ends of the T-handles. Finger grips are provided on the upper-rod assembly to allow the surgeon to easily use one hand to either apply or monitor the force acting along the upper-rod.

21 Claims, 3 Drawing Sheets

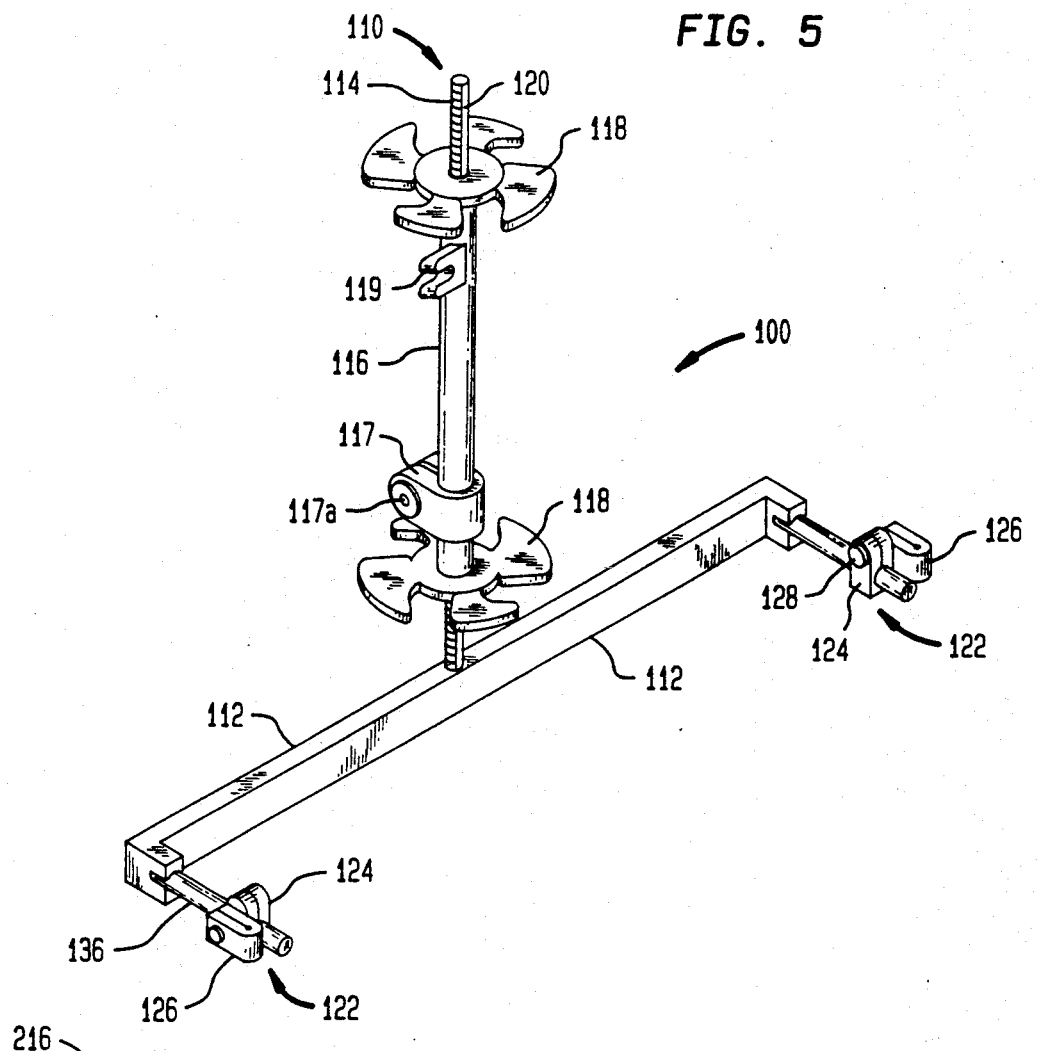
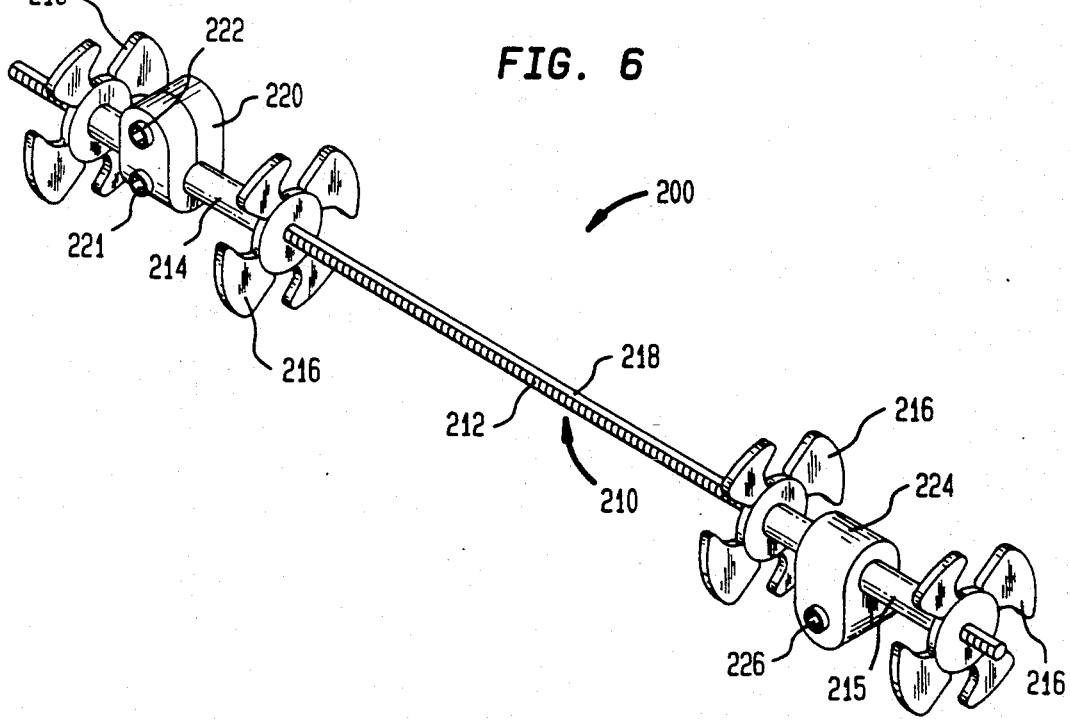

SPINAL FIXATOR REDUCTION FRAME

TECHNICAL FIELD

The present invention relates to devices for use in spinal fixation operations and more particularly to a device for controlled alignment of a fractured spine in conjunction with the Vermont Spinal Fixator implant.

BACKGROUND OF THE INVENTION

Although not part of the present invention, a basic understanding of the Vermont Spinal Fixator is important to the understanding of the present invention. FIG. 1 illustrates one half of a Vermont Spinal Fixator device 10 in place on a spine, the same components are also used on the opposite side of the spine and are not shown. The fixator device is designed to rigidly fix together two spinal vertebrae surrounding a fractured vertebrae and, thus, fuse the spine around the fractured vertebrae. The Vermont Spinal Fixator is disclosed in detail in Krag et al., *An Internal Fixator for Posterior Application to Short Segments of the Thoracic, Lumbar, or Lumbosacral Spine,* Clinical Orthopaedics and Related Research, 203: 75-98 (February 1986).

In order to implant the fixator device 10, holes are drilled in the appropriate vertebrae through the pedicle on either side of each vertebrae. After the holes are drilled, pedicle screws 12 are screwed into place using a shaft handle 14 which is attached to flats 16 provided on the top of each screw 12. The shaft handles 14 are best seen in FIG. 2. Once the pedicle screws 12 are in place, each one has an articulating clamp 18 attached to it by means of a clamp bolt 20.

Clamp bolt 20 is placed through clamp 18 and loosely threaded into the head of pedicle screw 12. The clamp bolts 20 are left loose until realignment of the vertebrae by the reduction frame has been completed. Shaft handles 14 remain attached to the tops of the pedicle screws 12. The shaft handles may be provided with removable grips which are not shown in FIG. 2.

As a result of various spinal disorders of the type which the fixator device 10 is intended to remedy, such as trauma, one vertebra is displaced to an abnormal position relative to an adjacent vertebra. For this reason the surgeon must manipulate the vertebrae back into normal alignment before the clamp bolts 20 are finally tightened and the spine is rigidly fixed in position.

In the past, in order to place the spine in proper alignment, the surgeon would either move the lower half of the patient's body with respect to the upper half, or would grasp the shaft handles 14 and use them as separate levers to manipulate the spine.

These procedures have a number of disadvantages. First, they not allow for fine control of the alignment and force applied, and also require the surgeon to hold the spine exactly in alignment while the clamp bolts are tightened. Second, when the handles are grasped and pushed together manually to produce extension, a compressive force is also produced. This compressive force is difficult to prevent manually and can cause bone fragments to be pushed posteriorly against the spinal cord. Third, while flexion and extension of the spine are generally possible with this technique, distraction (the in-line spreading apart of the spine) and compression are difficult, if not impossible, to achieve with accuracy and control. The difficulty arises due to the fact that the shaft handles act as levers on the spine, thereby tending to cause rotation of the vertebrae, which may not be desired. Fourth, there is a danger that excessive force may be applied to either the right or left pedicle screw during the application of force for accomplishment of realignment. This danger is present because of the absence of a rigid linkage between the right and left pedicle screws to provide an automatic balancing of forces.

There are a number of implants and reduction frame type devices in the prior art. However, none of them overcome the above disadvantages, at least without creating other disadvantages. For example, U.S. Pat. No. 3,865,105 to Lode discloses a device for exerting force on and fixing the spinal column. The Lode device appears to be designed primarily for the correction of scoliosis. The arrangement of this device renders it impractical for use in producing realignment of vertebrae affected by fractures and dislocations. The amount of control provided is limited as it is much less of a factor in applications such as straightening an unfractured spine contemplated by the Lode device. Also, the three point attachment directly to the transverse process or spinous process would obstruct the surgical area such that a spinal fixator device being implanted could not be easily accessed.

U.S. Pat. Nos. 4,433,677; 4,658,809 and 4,854,304 all show spinal fixation devices which are adjustable for distraction and compression. These all exhibit the primary disadvantage of not allowing flexion-extension adjustment which is often necessary for alignment of various spinal disorders including fractures and dislocations. These devices also generally employ turnbuckle type adjustments which are difficult to use under surgical conditions and do not offer significant mechanical advantage.

SUMMARY OF THE INVENTION

It is therefore an object of the present invention to provide a device for producing realignment of vertebrae affected by various spinal disorders, including fractures and dislocations, which device employs a significant mechanical advantage.

Another object of the present invention is to provide such a device which may be attached to the spine in any orientation prior to alignment.

Another object of the present invention is to provide a device for alignment of the spine which does not block access to the surgical area in order to allow for access to the fixator device being implanted.

It is also an object of the present invention to provide a device for alignment of a spine which distributes the applied force evenly across the screws and pedicles to which it attaches.

Yet another object of the present invention is to provide a versatile device which may be used with hand application of forces and varying degrees of mechanical assistance.

A further object of the present invention is to provide a device for alignment of a spine which is capable of controlling all modes of motion, that is, flexion/extension, lateral bending, axial rotation, distraction/compression, anterior/posterior shear, and lateral shear.

A further object of the present invention is to provide a device for alignment of a spine which includes a mechanical means for producing the motions of flexion/extension, distraction/compression, and anterior/posterior shear.

These and other objects are achieved by a reduction frame according to the present invention which is secured by shaft clamp assemblies to shaft handles extending from the pedicle screws of a fixator device. The shaft clamp assemblies are provided with four degrees of freedom (3 rotational and 1 translational). The shaft clamp assemblies secure two T-handles to the shaft handles. Each T-handle may be grasped by hand to manually apply forces to the spine, or the two T-handles may be joined by a mechanically adjustable lower-rod assembly.

The lower-rod assembly provides a mechanism to produce controlled distraction/compression and provides a fulcrum about which manually-applied force to the T-handles will produce flexion/extension. The lower-rod assembly is joined to each T-handle by means of a lower-rod clamp, which is provided with 4 or 5 degrees of freedom (2 or 3 rotational and 2 translational).

Each T-handle is provided with power screw threads to allow for precise anterior/posterior translational control. The shaft clamps and lower-rod clamps are provided with taper fit joints to allow for infinite rotational adjustment and fixture.

For further mechanical control, an upper-rod assembly may also be attached to the T-handles as desired. By rotating either nut on the upper-rod assembly, the distance between the upper ends of the T-handles may be increased or decreased. This will cause the T-handle to rotate about its lower-rod clamp, thereby rotating the vertebra to produce the desired alignment. Finger grips are provided on the upper-rod assembly to allow the surgeon to easily use one hand to either apply or monitor the force acting along the upper-rod.

The reduction frame according to the present invention allows for the controlled application of forces to produce motion of one vertebra relative to another, by means of attachment of the device to the pedicles. The T-handles function as handles to allow manipulation of the spine with an even distribution of force between opposite pedicles, in order to prevent the application of excessive load to either pedicle. The power screw adjustments allow for a fine and gradual application of force to produce the desired vertebral movements. The multiple degrees of freedom of the clamps allow for assembly of the reduction frame in any orientation and for forces to be applied in virtually any direction. The T-handles are offset from the surgical area by hinged extensions to allow for easy access to the device assembly device after alignment has been achieved, in order to allow for final fixation and tightening of the clamp bolts.

BRIEF DESCRIPTION OF THE DRAWINGS

The features and advantages of the present invention will be more readily apparent from the following detailed description of the invention illustrated in the drawing figures, wherein:

FIG. 5 is a perspective view of a T-handle of the present invention; and

FIG. 6 is a perspective view of the lower-rod assembly of the present invention.

DETAILED DESCRIPTION OF THE INVENTION

Figure 3:
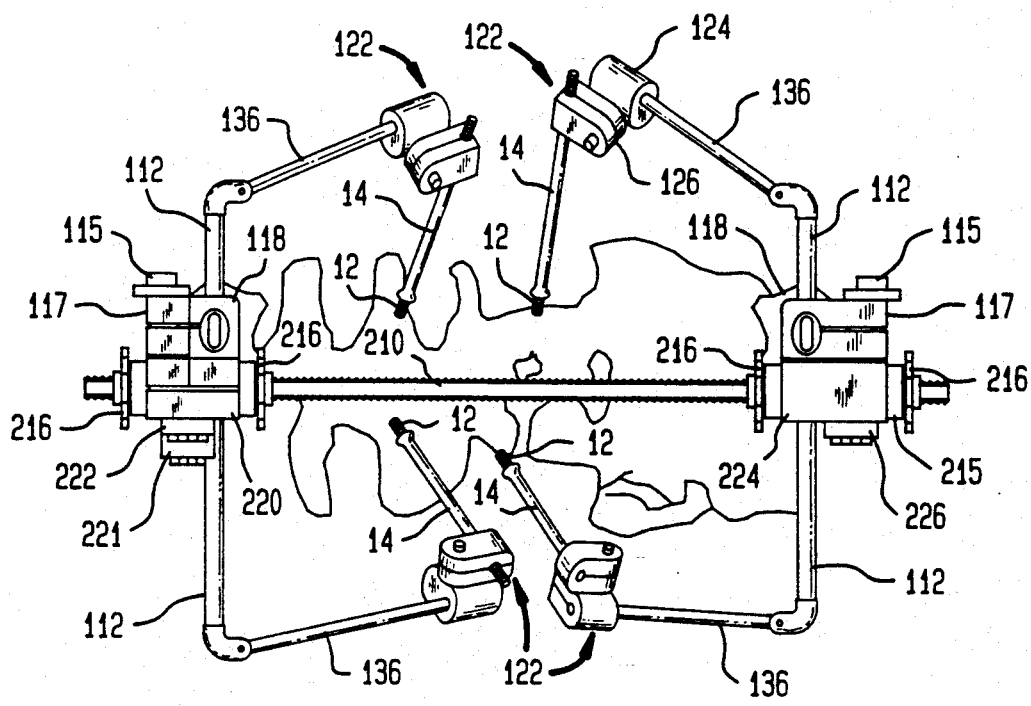
FIG. 3 is a section view through line 3—3 of FIG. 2.
Figure 2:
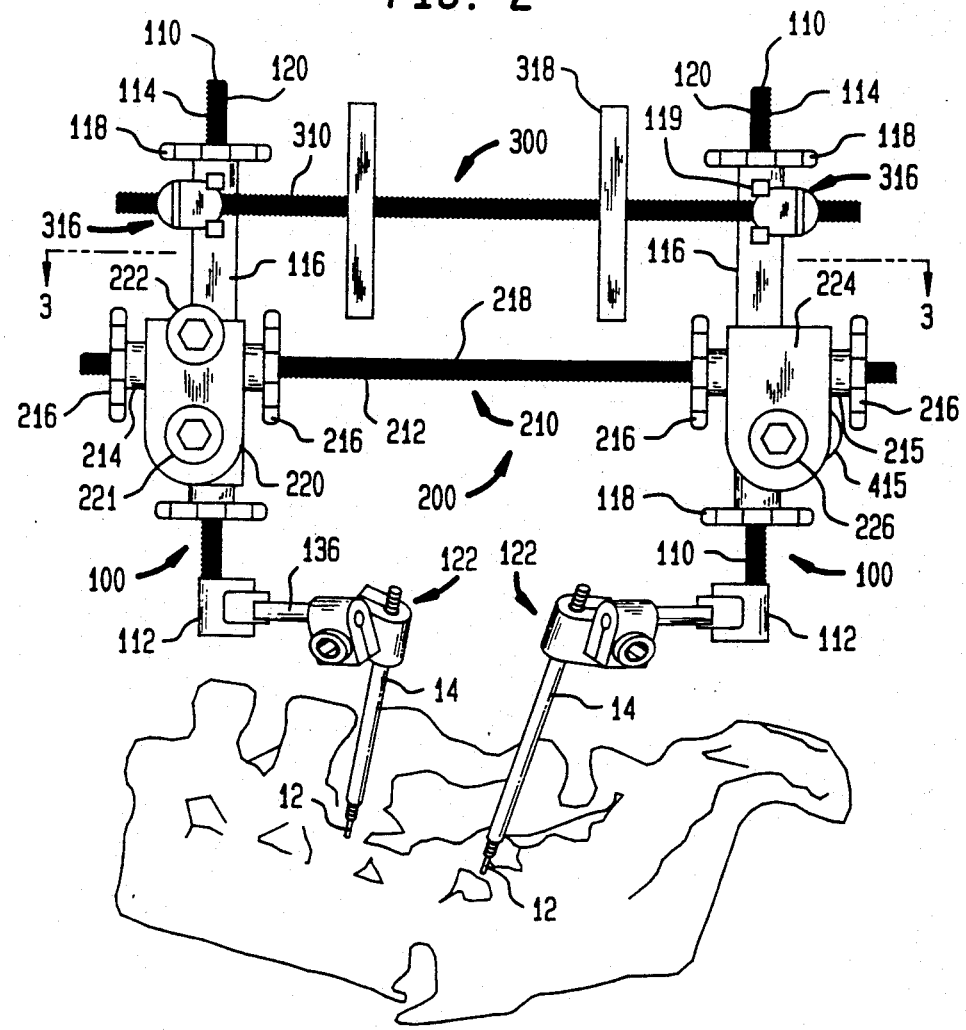
FIG. 2 is a side elevation of the reduction frame according to the present invention.

Referring to FIGS. 2 and 3 it can be seen that the reduction frame 50 according to the present invention comprises three basic assemblies: T-handles 100, of which there are two; lower-rod assembly 200; and upper-rod assembly 300. One T-handle 100 is shown separately in FIG. 5 and lower-rod assembly 200 is shown separately in FIG. 6. It should be understood that the upper and lower-rod assemblies are not necessarily required for the proper functioning of the invention. As will become apparent, depending on the degree of control desired by the surgeon, the T-handles 100 may be used alone, with the lower-rod assembly 200 only, or with the upper and lower-rod assemblies 300, 200.

Each T-handle 100 has a dorsally extending threaded leg 110 and two laterally extending arms 112. The dorsal direction is indicated by arrow 30 in FIG. 2 and the lateral directions by arrow 32 in FIG. 3. Threaded leg 110 is provided with power screw threads 114. A sleeve 116 is placed over the dorsally extending leg 110 and its dorsal-ventral location is controlled by thumb nuts 118. The leg 110 may be provided with a flat side 120 cooperating with a complimentary flat inside sleeve 116 to prevent undesired rotation of the sleeve 116. Disposed on sleeve 116 are female clamping collar 117 and eye socket 119. Female clamping collar 117 is rotatable around sleeve 116. Clamping collar 117 may be fixed against rotation by tightening screw 115, shown best in FIG. 3. The function of the sleeve 116 is related to the lower-rod assembly 200 and therefore will be discussed below in conjunction with that component. Eye socket 119 receives ball nuts 316 of upper-rod assembly 300.

Disposed adjacent the outer extremity of each laterally extending arm 112 is a shaft clamp 122. The shaft clamps provide a positive linkage between the T-handles 100 and the shaft handles 14 attached to the pedicle screws 12. The orientation of the shaft handles 14 extending from the pedicle is dependent upon the orientation of the vertebrae prior to alignment. Therefore, it must be possible to attach the T-handles 100 to the shaft handles 14 in any orientation. For this reason the shaft clamps 122 provide for three rotational degrees of freedom and one translational degree of freedom along shaft handles 14.

In order to allow for further flexibility in positioning the T-handles 100 and, in particular, to provide greater access to the surgical area after the reduction frame has been installed on the spine, the laterally extending arms 112 of the T-handles 100 have hinged extensions 136. Thus, in a preferred embodiment of the present invention, the shaft clamps 122 are disposed at the end of the hinged extensions 136 of the laterally extending arms 112.

Figure 4:
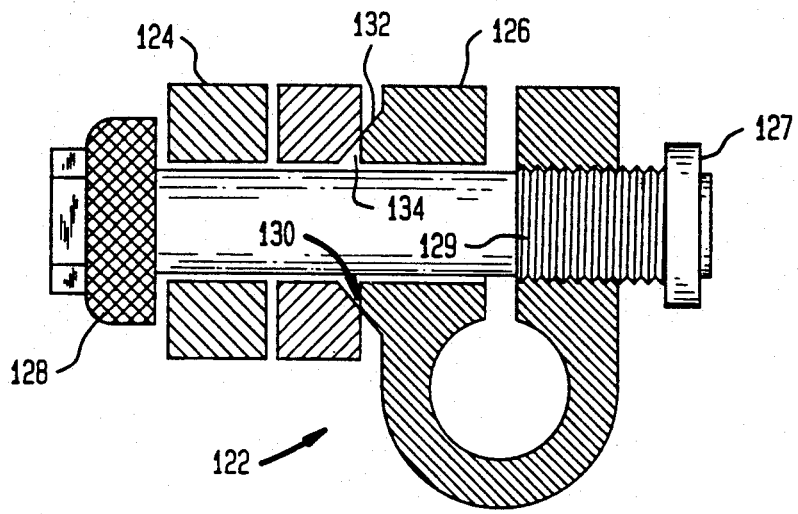
FIG. 4 is a partial section view of a shaft clamp of the present invention.

Shaft clamps 122, shown in detail in FIG. 4, comprise two U-shaped collars 124, 126 which are clamped together by a bolt 128 and retained by internal threads 129 in collar 126. A retaining ring 127 may be provided on bolt 128 to prevent the bolt from backing out of collar 126. Internal taper fit joint 130 is provided between the two collars 124, 126 of a shaft clamp 122 in order to allow for infinite positioning and positive fixation. To create the taper fit joint 130, collar 126 is formed with frustoconical projection 132 and collar 126 with a mating frustoconical recess 134 of slightly smaller dimension. Tightening of bolt 128 increases the interference fit and provides positive fixation. Loosening of bolt 128 allows slippage between the mating frustoconical parts 132, 134 which may then be placed in an infinite number of positions because the mating surfaces are smooth.

The T-handles 100 of the present invention provide a positive linkage between the two pedicles to which it is attached. The linkage ensures that force applied is evenly distributed to the two pedicles, thereby decreasing the likelihood of damage to any one pedicle. Once the T-handles 100 have been installed as described above, they may be used by the surgeon simply as handles for manual manipulation of the spine without assembling further components of the present invention. Such a procedure might be appropriate when only minor adjustments of the spine are required.

If the nature of the misalignment is such that it can not be easily or safely accomplished manually with only the T-handles 100, then the lower-rod assembly 200 may be installed. Lower-rod assembly 200, shown separately in FIG. 6, comprises a rigid lower threaded rod 210 of sufficient length to extend between and beyond the dorsally extending legs 110 of the T-handles 100 when they are installed on the spine in their usual configuration. Power screw threads 212 are also used for threaded rod 210. Placed over and slidable on threaded rod 210 are lower-rod sleeves 214 and 215. Translation and fixation of the lower-rod sleeves on threaded rod 210 are controlled by thumb nuts 216. Threaded rod 210 is also preferably provided with a flat side 218 engaging a complimentary flat inside the lower-rod sleeves to prevent undesired rotation.

Lower-rod sleeve 214 is linked to one of the T-handle sleeves 116 by male clamping collar 220 which cooperates with an associated female clamping collar 117. Female clamping collar 117 has a frustoconical recess 117a which mates with a frustoconical projection of male clamping collar 220 to provide a frustoconical taper fit joint similar to taper fit joints 130 in shaft clamps 122. Tightening of the taper fit joint between collars 117 and 220 is accomplished by bolt 221.

Flat side 218 on rod 210 prevents relative rotation between collars 214 and 215. Therefore, to allow opposite T-handles 100 to be angled with respect to each other when lower-rod assembly 200 is utilized, male clamping collar 220 is free to rotate around sleeve 214. The rotation is controlled by screw 222 which causes male clamping collar 220 to tighten on sleeve 214.

Lower-rod sleeve 215 is linked to the opposite T-handle 100 by male member 224 which is formed integrally with sleeve 215. Male member 224 also has a frustoconical projection which is received in frustoconical recess 117a of the associated female clamping collar 117. Bolt 226 controls the tightening of the taper fit joint formed between male member 224 and female clamping collar 117.

The arrangement of lower-rod assembly 200 effectively provides for rigid connection between T-handles 100 and lower-rod assembly 200, while providing five degrees of freedom for adjustment: two rotational degrees of freedom provided by clamping collars 117 around sleeves 116 and around their taper fit joints with clamping collars 220, 224; one rotational degree of freedom provided by male clamping collar 220 and sleeve 214; and two translational degrees of freedom provided by the movement of T-handle sleeves 116 or threaded leg 110 and lower-rod sleeves 214 and 215 on threaded rod 210.

With the lower-rod assembly 200 installed on the T-handles 100, the surgeon may execute any of the common movements of the spine (flexion, extension, distraction, compression or anterior/posterior shear) with a high degree of mechanical control. For example, all rotational degrees of freedom may be fixed and only translation along lower-rod assembly 200 utilized. This would provide a pure distraction-compression movement. The movement can be controlled with great precision by the use of thumb nuts 216. Alternatively, all degrees of freedom may be fixed except for one rotational degree of freedom between T-handles 100 and lower-rod assembly 200 about a transverse or side-to-side axis. This would provide a pure flexion-extension movement by force applied manually to the dorsally extending legs 110 of the T-handles 100. It should be readily appreciated that by employing the various adjustments available with the reduction frame according to the present invention, an infinite variety of controlled compound movements may be devised as required to align the fractured spine.

Even greater mechanical control may be achieved by the additional use of upper-rod assembly 300. The upper-rod assembly 300 comprises a threaded rod 310 of about the same length as the lower threaded rod 210, although it may be relatively smaller in diameter because it experiences only tensile and compressive forces. The threads 312 on the upper-rod assembly 300 are again preferably power screw threads. The upper-rod 310 runs through eye sockets 119 on T-handle sleeves 116 and ball nuts 316 bear against the eyes 119 to apply force to the T-handles 100. Finger grips 318 may be provided on the upper-rod 310 to provide a means for the surgeon to feel the amount of force required for a particular movement. To do so, the surgeon places T-handle sleeve 116 in his palm and then wraps his fingers around finger grip 318, whereby a squeezing motion gradually applies an inward force to the ends of the T-handles 100 (moving the handles together). The use of ball nuts 316 allows for fine mechanical control of movements such as the flexion-extension movement described in the preceding paragraph.

Figure 1:
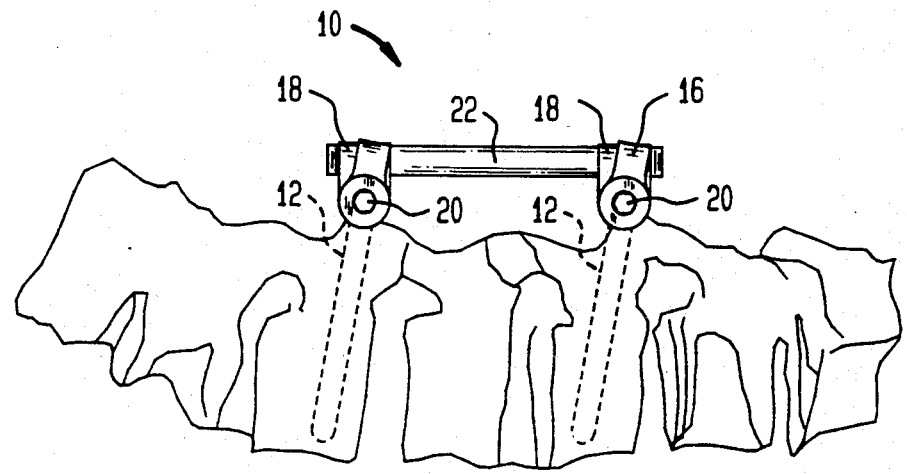
FIG. 1 is a side view of a spine with a Vermont Spinal Fixator implanted thereon.

The invention has been described above with reference to the Vermont Spinal Fixator device shown in FIG. 1. However, with only minor modifications depending on the particular device, the invention may be utilized with any spinal fixation device which employs at least four points of attachment to the spine, similar to the Vermont Spinal Fixator. Such modifications are well within the ability of a person of ordinary skill in the art based on the disclosure contained herein. Illustrative examples of such devices are contained in the following publications: W. Dick, The "fixateur interne" As a Versatile Implant for Spine Surgery, Spine 12:882-900, 1987; Olerud et al., Transpedicular Fixation of Thoracolumbar Vertebral Fractures, Clinical Orthopaedics and Related Research 227:44-51, 1988; and Guyer et al., The Wiltse Pedicle Screw Fixation System, Orthopaedics 11:1455-1460, 1988.

The detailed description of the invention contained herein is intended to in no way limit the scope of the invention. As will be apparent to a person skilled in the art, various modifications and adaptations of the structure above described will become readily apparent without departure from the spirit and scope of the invention, the scope of which is defined in the appended claims.

What is claimed is:

1. A device for producing realignment of vertebrae affected by various spinal disorders, including fractures and dislocations, wherein vertebrae adjacent to and on opposite sides of the affected location are provided with two generally dorsally extending screws, one screw on each side of the spinous process, said device comprising two members configured and dimensioned to extend laterally and dorsally with respect to the spine, wherein each of said members are T-shaped and comprise a central dorsally extending leg, two laterally extending arms and a hinged extension member pivotably connected to the outer end of each arm, said members further include means for rigidly linking the two screws provided in one vertebrae comprising clamping members disposed on said hinged extension members for clampingly engaging the vertebrae screws or extensions thereof and spacing the dorsally extending leg away from said screws, said dorsally extending legs thereby providing handles for manipulation of the spine.

2. A device for producing realignment of vertebrae affected by various spinal disorders, including fractures and dislocations, wherein vertebrae adjacent to and on opposite sides of the affected location are provided with two generally dorsally extending screws, one screw on each side of the spinous process, said device comprising:
two members configured and dimensioned to extend laterally and dorsally with respect to the spine, each of said members including means for rigidly linking the two screws provided in one vertebrae, thereby providing handles for manipulation of the spine;
first adjustable means for alternately rigidly connecting the laterally and dorsally extending members and providing controlled mechanical alignment of the spine by moving said members; and
means for controlled, generally dorsal-ventral translation of said first adjustable means along one or both dorsally extending members.

3. The device according to claim 2 wherein said first adjustable means comprises:
a rigid threaded member;
two clamping members slidable on said rigid member, one each clampingly engaging one of the dorsally extending members; and
screw means associated with each clamping member for alternately providing controlled translational movement of said clamping members along said threaded member and fixing said clamping members at desired positions.

4. The device according to claim 3 wherein at least one of the clamping members clampingly engage the dorsally extending members with three possible rotational degrees of freedom.

5. The device according to claim 2, further comprising means, disposed on each laterally and dorsally extending member, for controlled, generally dorsal-ventral translation of the connection points between the dorsally extending members and said first adjustable means.

6. The device according to claim 5, wherein:
the laterally and dorsally extending members are T-shaped, each having a central, dorsally extending threaded leg and two laterally extending arms;
said dorsal-ventral translation means comprises.
a sleeve slidable on the threaded leg and connected to the first adjustable means, and
screw means associated with each sleeve for alternately providing controlled translational movement of said sleeves along the threaded legs and fixing said sleeves at a desired position; and said dorsally extending members further comprise
hinged extensions of said laterally extending arms, and
clamping members disposed on said hinged extensions for clampingly engaging the vertebrae screws or extensions thereof.

7. The device according to claim 6, wherein the clamping members clampingly engage the vertebrae screws or extensions thereof with three possible rotational degrees of freedom.

8. The device according to claim 2, further comprising second adjustable means for linking the laterally and dorsally extending members and for applying controlled force on said members to rotate said members about the connection point of said first adjustable means.

9. The device according to claim 8, wherein the second adjustable means comprises:
a threaded rod; and
nut members disposed on said threaded rod and bearing against the dorsally extending members, whereby rotation of said nut members allows infinitely controllable application of force to the dorsally extending members thereby causing rotation about the connection point of the first adjustable means and thus transmission of the force to the vertebrae.

10. The device according to claim 9, wherein the second adjustable means further comprises finger grips disposed on the threaded rod for facilitating manual application of force and human sensitivity to force applied.

11. A device for the realignment of a dislocated spine, comprising:
two rigid members, each member removably attachable to the spine in a dorsally extending orientation on either side of the dislocation, each member including means for attaching said member to a single vertebrae at two points, one point on each side of the spinous process;
first adjustable means installable on said rigid members for linking said rigid members when attached to the spine, including threaded means for alternately providing a rigid connection between said members and mechanically applying controlled forces to said members, said first adjustable means including means for cooperating with said rigid members alone to provide pure distraction-compression forces on the spine; and
second adjustable means installable on said rigid members for mechanically applying controlled forces to said rigid members, said second means disposed dorsally with respect to said first means when said rigid members are attached to the spine, whereby the spine may be aligned with varying degrees of mechanical control by selectively installing and utilizing said first and second means;
wherein said rigid members each include means for controlled, generally dorsal-ventral translation of said first and second adjustable means when installed thereon.

12. The device according to claim 11 wherein said first adjustable means comprises:
a rigid threaded member;
two clamping members freely slidable on said threaded member, one each clampingly engaging one of the dorsally extending members; and screw means associated with each clamping member for alternately providing controlled translational movement of said clamping members along said threaded member and fixing said clamping members at desired positions.

13. The device according to claim 11, wherein the second adjustable means comprises:
a threaded rod;
nut members disposed on said threaded rod and bearing against the dorsally extending members, whereby rotation of said nut members allows infinitely controllable application of force to the dorsally extending members thereby causing rotation about the linkage point of the first adjustable means and thus transmission of force to the spine; and
finger grip means disposed on said threaded rod for facilitating manual application of force and human sensitivity to force applied.

14. An apparatus, comprising:
a T-shaped rigid member having a threaded leg and two arms;
extension members pivotally connected to an end of each of said arms; and
two clamp members, one each clampingly engaging one extension members opposite the pivotable connection, said clamp members each separately capable of additionally clampingly engaging a shaft-like member at an orientation different from the orientation said extension members with respect to said apparatus.

15. The apparatus according to claim 14, further comprising:
a first sleeve member with two ends disposed on said threaded leg and slidable thereon;
two nuts disposed on said threaded leg, one each adjacent an end of said first sleeve member whereby selective rotation of said nuts alternately provides translation or fixation of said sleeve member on said threaded leg;
a rigid threaded rod;
a second sleeve member with two ends disposed on said threaded rod and slidable thereon;
two nuts disposed on said threaded rod, one each adjacent an end of said second sleeve member whereby selective rotation of said nuts alternately provides translation or fixation of said second sleeve member on said threaded rod; and
a clamp member having two clamping collars rotatable with respect to each other, one collar clampingly engaging said second sleeve and the other collar clampingly engaging said first sleeve.

16. The apparatus according to claim 15, further comprising:
an eye socket extending from the first sleeve;
a second threaded rod; and
a nut disposed on said second threaded rod and bearing against said eye socket.

17. The apparatus according to claim 16, wherein:
said two clamp members clampingly engaging said extension members each comprise two clamping collars rotatable with respect to each other; and
all clamp members having two collars have one collar provided with a frustoconical projection and a second collar defining a complimentary frustoconical recess for receiving said projection with an interference fit.

18. An apparatus, comprising:
two T-shaped rigid members, each having a threaded leg and two arms;
extension members pivotally connected to an end of each of said arms;
four first clamp members, each having two clamping collars rotatable with respect to each other, one member each clampingly engaging one of said extension members opposite the pivotable connection, said first clamp members each separately capable of additionally clampingly engaging a shaft-like member at an orientation different from the orientation of said extension members with respect to said apparatus;
two first sleeve members each with two ends, one sleeve member disposed on each of said threaded legs and slidable thereon;
two nuts disposed on each said threaded leg, one each adjacent an end of each said first sleeve members whereby selective rotation of said nuts alternately provides translation or fixation of said first sleeve members on said threaded legs;
a rigid threaded rod extending between said T-shaped members;
a second sleeve member and a third sleeve member each with two ends disposed on said threaded rod and slidable thereon;
four nuts disposed on said threaded rod, one each adjacent an end of one of said second and third sleeve members whereby selective rotation of said nuts alternately provides translation or fixation of said second and third sleeve member on said threaded rod;
a second clamp member, having two clamping collars rotatable with respect to each other, one collar clampingly engaging said second sleeve and the other collar clampingly engaging one first sleeve;
a clamping collar clampingly engaging the other first sleeve and cooperating with said third sleeve in a manner alternately allowing rotation and fixation;
an eye socket extending from each first sleeve member;
a second threaded rod extending between the T-shaped members; and
two nuts disposed on said second threaded rod, one each bearing against said eye sockets.

19. A method for realigning vertebrae affected by various spinal disorders including fractures and dislocations, comprising:
installing generally dorsally extending screws in the pedicles of vertebrae adjacent to and on opposite sides of the affected location, whereby a vertebra on a first side of the affected location has two screws one in each pedicle, and a vertebra on a second side of the affected location has two screws, one in each pedicle;
rigidly linking the two screws installed in the pedicles of each vertebra by securing a rigid member therebetween, said rigid members each having a portion extending laterally between the screws and a dorsally extending portion;
manipulating the spine into alignment by applying forces to said rigid members;
fixing the dislocation or fracture in the aligned position by linking the screws in opposite vertebra with fixation means; and
removing said rigid members while leaving said fixation means in place.

20. The method according to claim 19, further comprising:

connecting said rigid members with a first adjustable means including a rod extending between said rigid members, wherein said connection alternately provides both relative movement between each rigid member and the rod, and rigid fixation of the rod to the rigid members;

selectively applying force to the vertebrae to align the vertebrae by moving at least one said rigid member relative to the rod; and rigidly linking the rigid members with said first adjustable means when the vertebrae are in alignment.

21. The method according to claim 20, further comprising:

mounting a second adjustable means on the rigid members dorsally with respect to the first adjustable means, said second adjustable means including a threaded rod extending between the rigid members with nut members disposed on the threaded rod bearing against dorsally extending portion; and applying force to the vertebrae by turning at least one nut member on the second adjustable means to rotate the rigid members around the connection to the first adjustable means.

* * * * *